United States Patent
Bjellqvist et al.

(10) Patent No.: US 8,187,438 B2
(45) Date of Patent: May 29, 2012

(54) USE OF AN ELECTROPHORETIC GEL PROVIDED WITH A NON-ADHERENT POLYMER FILM

(75) Inventors: Bengt Bjellqvist, Stockholm (SE); Sofia Edlund, Uppsala (SE); Jesper Hedberg, Stockholm (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 350 days.

(21) Appl. No.: 12/438,205

(22) PCT Filed: Sep. 24, 2007

(86) PCT No.: PCT/SE2007/000837
§ 371 (c)(1),
(2), (4) Date: Feb. 20, 2009

(87) PCT Pub. No.: WO2008/039128
PCT Pub. Date: Apr. 3, 2008

(65) Prior Publication Data
US 2010/0243453 A1    Sep. 30, 2010

(30) Foreign Application Priority Data
Sep. 26, 2006  (SE) ..................................... 0602008

(51) Int. Cl.
*G01N 27/447* (2006.01)
*G01N 27/453* (2006.01)
(52) U.S. Cl. ....................................... 204/466; 204/616
(58) Field of Classification Search .................. 204/456, 204/466, 606, 616
See application file for complete search history.

(56) References Cited

U.S. PATENT DOCUMENTS
2002/0056639 A1   5/2002 Lackritz et al.

FOREIGN PATENT DOCUMENTS
| WO | WO02/08744 | 1/2002 |
| WO | WO2004/106911 | 12/2004 |
| WO | WO2006/057601 | 6/2006 |

OTHER PUBLICATIONS

Li, C., et al., "Isoelectric focusing in cyclic olefin copolymer microfluidic channels coated by polyacrylamide using a UV photografting method", Electrophoresis, 2005, 26, 1800-1806.

*Primary Examiner* — J. Christopher Ball

(57) ABSTRACT

This invention relates to electrophoresis, in particular precast mini gels with a low fluorescent polymer backing that is not adherent to the gel. Use of this type of small gel simplifies blotting procedures, such as Southern and Western blotting, after electrophoresis.

5 Claims, No Drawings

USE OF AN ELECTROPHORETIC GEL PROVIDED WITH A NON-ADHERENT POLYMER FILM

CROSS-REFERENCE TO RELATED APPLICATIONS

This application is a filing under 35 U.S.C. §371 and claims priority to international patent application number PCT/SE2007/000837 filed Sep. 24, 2007, published on Apr. 3, 2008, as WO 2008/039128, which claims priority to patent application number 0602008-5 filed in Sweden on Sep. 26, 2006.

FIELD OF THE INVENTION

This invention relates to electrophoresis, in particular pre-cast mini gels with a backing that is not adherent to the gel. Use of this type of small gel simplifies blotting procedures after electrophoresis.

BACKGROUND OF THE INVENTION

Gel electrophoresis is one of the most common methods for rapid and simple protein analysis.

Electrophoresis has been used for a long time to separate charged molecules according to their difference in migration rate under the influence of an electrical field. An electrophoresis system is standard equipment in almost every lab in the world.

Traditionally, the molecules are stained in the gel after electrophoresis by more or less selective dye stains or by precipitation of colloidal metal particles.

The molecules to be separated may also be labelled with, for example a radioactive or fluorescent label, for detection after the electrophoresis.

Today it is most common to avoid the use of radioactivity in favour of fluorescent labelling. However, the electrophoretic backings used to carry the electrophoretic slab gel are in many cases fluorescent per se which disturbs the detection procedure.

Commonly used electrophoretic support films, such as polyethylene terephthalate (PET) comprise an adhesive layer between the support film and the hydrogel. This type of backed gels, for example PHAST™ gels, function satisfactorily for relatively large amounts of fluorescence labelled biomolecules but their inherent fluorescence is too high which disturbs and hinders the detection of low amounts of biomolecules after slab gel electrophoresis.

Since this can lead to false negative results in for example a diagnostic assay it is very important to be able to detect very low amounts of biomolecules in for example a biological sample. Another case is in pharma research where most of the pharmacologically interesting proteins occur at very low concentrations compared to high abundance proteins, such as plasma albumin.

It would be desirable to have a gel without backing for blotting applications, such as Western blot applications. PHAST™ gels are at the present possible to use in Western blot applications although with some difficulties. Since the gel is firmly attached to the plastic backing the gel needs to be removed from the backing using a "gel remover". This is not user friendly and introduces variability to the experiment.

To solve this problem, electrophoretic supports of glass have been used. Glass enables imaging of low amounts of fluorescence labelled samples. However, glass as electrophoretic support is not desirable of space, weight and safety reasons. Furthermore, electrophoretic glass supports are not suitable for production of large amounts of pre-swollen ready to use gels. It would be desirable to have pre-swollen ready to use gels which are non-fragile, enable fluorescence detection of low sample amounts and occupy a minimum of space.

Another solution to avoid the problem with fluorescent background in detection of fluorescence labelled electrophoresis samples, has been described in WO 04/106911. Here a low fluorescent polymer film is used so support the hydrogel. The hydrogel is attached to the polymer film by an adhesive layer. For performing Western blotting after electrophoresis, the polymer film has to be removed from the gel before the blotting procedure.

Thus, the detection problem with fluorescence labelled biomolecules following slab gel electrophoresis and the transferring problem thereafter to Western blotting still need to be solved.

SUMMARY OF THE INVENTION

This invention relates to pre-cast mini gels which are cast and polymerised on "naked" film. With "naked" film means that the film is not coated with anything for gel adhesion, such as alkylglycidyl agarose. The gel can easily be peeled off the backing after electrophoresis and thus a backing which could potentially disturb the sample detection is no longer present. The gels are especially suited for blotting onto membranes for blotting applications, such as Western or Southern blotting.

Although the gel is not covalently attached to the plastic backing, it is still strong enough to withstand standard flatbed electrophoresis procedures due to the small format of the gel.

Thus, in a first aspect the invention relates to use of an electrophoretic gel provided with a non-adherent polymer film for electrophoresis and subsequent blotting, wherein the non-adherent polymer film is selected from a polymer having the following formula:

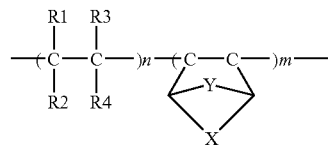

wherein
n=0-100 000
m=0-100 000
R1, R2, R3 and R4=H, F, Cl, Br, I, methyl groups or non-aromatic hydrocarbon chains (optionally containing branches or cyclic structures) such as ethyl, ethenyl, propyl, isopropyl, propenyl, butyl, branched butyl, butenyl, cyclobutyl, pentyl, branched pentyl, pentenyl, cyclopentyl, hexyl, branched hexyl, cyclohexyl;
X, Y=methylene groups or non-aromatic hydrocarbon chains (optionally containing branches or cyclic structures) such as ethylene, ethenylene, propylene, isopropylene, propenylene, butylene, branched butylene, butenylene; and
Y can optionally be absent.

The format of the electrophoretic gel according to the invention is critical and can be at most the following dimensions 150×150×1 mm.

A preferred format is 43×50×0.45 mm.

The electrophoretic gel according to the invention is a hydrogel selected from agarose, acrylamide or derivatised acrylamide.

In a preferred embodiment, the hydrogel is pre-cast on the polymer film.

Optionally, the electrophoretic gel is imaged before blotting.

DETAILED DESCRIPTION OF THE INVENTION

The gels according to the present invention are easy to peel off from the plastic backing. The small format enables easy handling of the gel not only for removal from the backing but also for blotting to a blotting membrane.

Samples on the minigel according to the invention may be detected by fluorescence after electrophoresis or may be directly blotted and the samples may be detected in blotting procedures only, for examples proteins may be detected by antibodies in the Western blotting procedure.

EXAMPLES

The present invention will be described in more detail by way of examples, which however are in no way intended to limit the scope of the present invention as defined by the appended claims. All references given below or elsewhere in the present specification are hereby included herein by reference.

A standard SDS-PAGE gel was cast on an untreated low fluorescent (LF) polymer film (ZEONOR™) by standard UV-polymerisation techniques. The gel had the following dimensions 43×50×0.45 mm.

Protein samples were fluorescently labelled with Cy5, Cy3 and Cy2 according to standard procedures and the protein samples were separated in the LF gel using standard equipment. The samples were detected by a fluorescence scanner after electrophoresis using a standard laser scanner.

Following electrophoresis, the gel was easily removed from the LF-support film and blotted over to a Western blotting membrane.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. An improved method for the separation and detection of a sample, which method comprises (a) separating said sample by gel electrophoresis; and (b) blotting and detecting separated sample; the improvement comprising using an electrophoretic gel provided in direct contact with a non-adherent polymer film for electrophoresis and subsequent blotting, wherein the polymer film is selected from a polymer having the following formula:

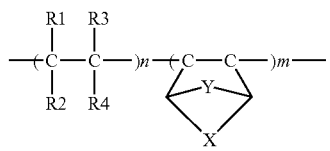

wherein
n=0-100 000
m=0-100 000
R1, R2, R3 and R4=H, F, Cl, Br, I, methyl groups or non-aromatic hydrocarbon chains (optionally containing branches or cyclic structures) such as ethyl, ethenyl, propyl, isopropyl, propenyl, butyl, branched butyl, butenyl, cyclobutyl, pentyl, branched pentyl, pentenyl, cyclopentyl, hexyl, branched hexyl, cyclohexyl;
X, Y=methylene groups or non-aromatic hydrocarbon chains (optionally containing branches or cyclic structures) such as ethylene, ethenylene, propylene, isopropylene, propenylene, butylene, branched butylene, butenylene;
Y can optionally be absent, wherein the format of the gel is at the most 150×150×1 mm.

2. The method of claim 1, wherein the electrophoretic gel is a hydrogel selected from agarose, acrylamide or derivatised acrylamide.

3. The method of claim 1, wherein the format is 43×50×0.45 mm.

4. The method of claim 1, wherein the electrophoretic gel is precast and ready to use.

5. The method of claim 1, wherein the electrophoretic gel is imaged before blotting.

\* \* \* \* \*